United States Patent
Wang (10) Patent No.: US 9,198,743 B2
(45) Date of Patent: Dec. 1, 2015

(54) UNITARY ALVEOLAR BONE CHISEL AND SPREADER OSTEOTOME FOR A DENTAL IMPLANT

(75) Inventor: Je-Won Wang, Daejeon-si (KR)

(73) Assignee: INNOBIOSURG CORPORATION, Daejeon (KR)

(*) Notice: Subject to any disclaimer, the term of this patent is extended or adjusted under 35 U.S.C. 154(b) by 467 days.

(21) Appl. No.: 13/254,371

(22) PCT Filed: Apr. 28, 2010

(86) PCT No.: PCT/KR2010/002667
§ 371 (c)(1),
(2), (4) Date: Sep. 1, 2011

(87) PCT Pub. No.: WO2010/128771
PCT Pub. Date: Nov. 11, 2010

(65) Prior Publication Data
US 2011/0306981 A1    Dec. 15, 2011

(30) Foreign Application Priority Data
May 4, 2009 (KR) .................. 10-2009-0038894

(51) Int. Cl.
A61B 17/16 (2006.01)
A61C 8/00 (2006.01)

(52) U.S. Cl.
CPC .................... *A61C 8/0089* (2013.01)

(58) Field of Classification Search
CPC ................................. A61B 17/1604
USPC ........... 606/79, 80, 83, 84, 85; 30/167–167.2, 30/299, 304, 347, 352, 353, 356; 433/144, 433/165
See application file for complete search history.

(56) References Cited

U.S. PATENT DOCUMENTS

| | | | | |
|---|---|---|---|---|
| 749,624 | A * | 1/1904 | McCullough | 433/165 |
| 3,076,356 | A * | 2/1963 | Simich | 408/223 |
| 3,583,390 | A * | 6/1971 | Jascalevich | 600/564 |
| 5,570,700 | A * | 11/1996 | Vogeler | 600/567 |
| 5,716,360 | A * | 2/1998 | Baldwin et al. | 606/80 |
| 5,915,893 | A * | 6/1999 | Miyanaga | 408/202 |
| 5,997,298 | A * | 12/1999 | Nowak | 433/165 |
| 6,179,839 | B1 * | 1/2001 | Weiss et al. | 606/281 |
| 6,702,822 | B1 * | 3/2004 | Noiles et al. | 606/89 |
| 6,890,133 | B2 * | 5/2005 | Singh et al. | 408/225 |
| 7,402,040 | B2 * | 7/2008 | Turri | 433/165 |

(Continued)

FOREIGN PATENT DOCUMENTS

| | | |
|---|---|---|
| KR | 10-2007-0119628 | 12/2007 |
| KR | 10-0821074 | 4/2008 |

(Continued)

*Primary Examiner* — Christian Sevilla
*Assistant Examiner* — Eric S Gibson
(74) *Attorney, Agent, or Firm* — Novick, Kim & Lee, PLLC; Jae Youn Kim

(57) ABSTRACT

Provided is an integrated alveolar bone dilating apparatus for dental implant. The apparatus includes a grip, a stopper, and a dilating part. The grip has a cylindrical shape. The stopper is disposed under the grip and has a diameter greater than a diameter of the grip. The dilating part is disposed under the stopper. Here, the dilating part includes a dilator reduced in diameter toward a lower portion thereof and having an inverted conic shape with a sharp tip, and two blades disposed on both sides of the dilator and being sharp toward the outside.

2 Claims, 6 Drawing Sheets

(3A)

(3B)

(56) References Cited

U.S. PATENT DOCUMENTS

| | | | |
|---|---|---|---|
| 8,202,141 B2 * | 6/2012 | Le Borgne et al. | 451/70 |
| 2002/0107521 A1 * | 8/2002 | Petersen et al. | 606/85 |
| 2005/0003327 A1 | 1/2005 | Elian et al. | |
| 2006/0111724 A1 * | 5/2006 | Yeung Wai Ping | 606/80 |
| 2006/0172255 A1 * | 8/2006 | Hochman et al. | 433/144 |
| 2007/0093896 A1 * | 4/2007 | Malinin | 623/14.12 |
| 2007/0099150 A1 | 5/2007 | Muller et al. | |
| 2007/0259314 A1 * | 11/2007 | Danger et al. | 433/165 |
| 2009/0142731 A1 * | 6/2009 | Kim | 433/165 |
| 2009/0162805 A1 * | 6/2009 | Berna | 433/3 |
| 2009/0305189 A1 * | 12/2009 | Scortecci et al. | 433/165 |
| 2012/0323243 A1 * | 12/2012 | Moon et al. | 606/80 |
| 2013/0144320 A1 * | 6/2013 | To | 606/190 |
| 2013/0218160 A1 * | 8/2013 | Bjorn et al. | 606/80 |
| 2013/0244202 A1 * | 9/2013 | Chen | 433/165 |

FOREIGN PATENT DOCUMENTS

| | | | |
|---|---|---|---|
| KR | 10-0630304 | 2/2009 | |
| KR | 10-0884211 | 2/2009 | |
| WO | WO 2006117298 A1 * | 11/2006 | A61C 8/00 |

* cited by examiner

FIG. 11

UNITARY ALVEOLAR BONE CHISEL AND SPREADER OSTEOTOME FOR A DENTAL IMPLANT

TECHNICAL FIELD

The present invention relates to an integrated alveolar bone incision dilating apparatus for dental implant, which integrates a bone chisel for incising an alveolar bone and a bone spreader osteotome that are a sort of surgical instruments for dental implant.

BACKGROUND ART

Generally, implants mean a substitute that replaces an original body tissue, but in dentistry, mean implanting an artificial tooth.

A dental root that is formed of titanium having no rejection symptom against a human body is implanted into an alveolar bone, and then an artificial tooth is fixed thereon to recover the function of the original tooth. In the case of general prostheses and dentures, surrounding teeth or bones are damaged over time, but in the case of implants, peripheral dental tissues are not damaged, and no caries arise while having the same function and shape as natural teeth. Accordingly, the implants can be used semi-permanently.

Generally, when implant is performed on an alveolar bone, there should be an alveolar bone wide enough to perform implant. When the width of the alveolar bone of a patient is too small to perform implant, the alveolar bone of the patient is incised by a chisel, and then a gap created by the chisel is expanded by a spreader or an osteotome to perform implant.

In this case, however, three different tools such as chisel, spreader, and osteotome are needed, and two or more different processes have to be performed. Also, since a great pressure is apt to be concentrated on one spot, lateral bone pieces may be fractured to fail to expand. In order to overcome the above limitations, many studies have been conducted.

For example, Korean Patent Publication No. 10-2007-0119628 discloses a new platform including a dental implant (1) and related parts. The dental implant (1) and the related parts have reduced diameters, and particularly, they are appropriate for a certain application for treating a fine width region of a bone peak. In order to obtain the dental implant (1) and the related parts that are for fine width type but are still strong and reliable, technology of re-adjusting and optimizing certain features and geometrical shape of the dental implant (1) and the related parts is disclosed.

Korean Patent Registration No. 10-0821074 discloses a bone tissue dilator for maintaining an expanded state of the bone tissue incised on an operation spot where dental implant is to be performed. The bone tissue dilator includes a support piece (20) with a through hole having a spiral groove on an inner circumferential surface, the support piece (20) being disposed parallelly to a device body (10), a fixing piece (30) with an insertion space (32) on the center thereof, the fixing piece (30) being disposed perpendicularly to the device body (10), an operation piece (40) inserted into the through hole (24) of the support piece (20) and having a spiral groove (42) on the outer circumferential surface thereof, engaged with a spiral groove (22) on the inner circumferential surface of the through hole (24), the operation piece (40) moving forward and backward in the through hole (24) as being revolved by a screw driver (60), and a movement expanding piece (50) inserted into the front side of the through hole (24) of the support piece (20) and disposed at the front side of an operation axis (52) interlocking with the operation piece (40), the movement expanding piece (50) being located on the same line as the fixing piece (30) in the insertion space (32) of the center of the fixing piece (30).

Korean Patent Registration No. 10-0630304 discloses a reamer for operating implant including an incision part that forms a hole for implant placement in a bone, and a connection part having a smaller diameter than that of the incision part and downwardly extending from the incision part. The incision part includes a projecting surface formed by upwardly protruding one side including the outer circumference among the whole surface of the top of the incision part such that a step is formed; a recessed surface formed by recessing one side of the whole surface of the incision part in contrast to the projecting surface and having an inverse inclination to the clockwise direction; a cut edge horizontally formed on a connection spot of the step and the projecting surface such that a cutting process is safely performed without a damage of a membrane of a sinus by uniformly distributing a strength while maintaining a horizontal line contact with the sinus; and a discharge passage formed by cutting from one side of the top of the incision part, i.e., a certain spot between the projecting surface and the recessed surface to a spot slightly distant from the bottom of the incision part.

Korean Patent Registration No. 10-0884211 discloses a piezotome for a sinus vertical approach operation. The piezotome includes a piezo body having one end fixedly inserted into a hand piece of a piezo main device, a piezo pole extending to the other end of the piezo body and having a linear or bent structure, and a piezo tip with a plurality of cutting blades at a uniform interval to perform cutting on the end portion of the piezo pole.

The plurality of cutting blades (14) of the piezo tip (13) is formed to have a semi-spherical shape in which each end portion converges toward the front end. A water supply hole (15) is formed in the center of the inside of the piezotome to pass through the piezo body (11), the piezo pole (12), and the piezo tip (13). A stopper (16) integrally protrudes from the outer circumferential surface of the piezo pole (12) to restrict an insertion distance according to the thickness of a remaining bone.

DISCLOSURE

Technical Problem

In the related-art method, when implant is performed on an alveolar bone, there should be an alveolar bone wide enough to perform implant. When the width of the alveolar bone of a patient is too small to perform implant, the alveolar bone of the patient is cut by a chisel, and then a gap created by the chisel is expanded by a spreader or an osteotome to perform implant. In this case, however, three different tools such as chisel, spreader, and osteotome are needed, and two or more different processes have to be performed. Also, since a great pressure is apt to be concentrated on one spot, side bone may be fractured to fail to expand.

Accordingly, the present invention provides an integrated alveolar bone incision dilating apparatus for dental implant, which integrates a bone chisel for cutting an alveolar bone and a bone spreader osteotome that are a sort of surgical instruments for implant.

Technical Solution

In one general aspect, an integrated alveolar bone dilating apparatus for dental implant includes: a grip having a cylindrical shape; a stopper disposed under the grip and having a diameter greater than a diameter of the grip; and a dilating part disposed under the stopper, wherein the dilating part comprises a dilator reduced in diameter toward a lower portion thereof and having an inverted conic shape with a sharp tip, and two blades disposed on both sides of the dilator and being sharp toward the outside.

Advantageous Effects

According to embodiments of the present invention, since only one tool integrating a chisel for cutting an alveolar bone and a dilator (spreader or osteotome) having an oval shaped diameter is used, it is possible to perform an economical and time-saving implant operation. Also, since excessive bone incision and fracture can be prevented, implant operation can be more effectively performed.

BEST MODE

Hereinafter, an implant operation using an integrated alveolar bone incision dilating apparatus for dental implant according an embodiment of the present invention will be described.

First, a tooth may be removed, and then a grip 1 of an integrated alveolar bone incision dilating apparatus for dental implant may be grasped by the hand. Thereafter, when a strength (pressure) is applied to the top of the grip 1 by a hammer, an alveolar bone may be incised by a blade 31 of a dilator, and simultaneously, the incised alveolar bone may be expanded by a dilating part 32, 32-1, 32-2, 32-3 and 32-4 of the dilator 3, 3-1, 3-2, 3-3 and 3-4. When the alveolar bone is expanded to a certain width, an implant may be fixed in the expanded part, and other surrounding bones may be transplanted and arranged to perform an implant operation.

MODE FOR INVENTION

In order to achieve the above purpose, the present invention provides an integral alveolar bone dilating apparatus for dental implant including a grip 1 having a cylindrical shape, a stopper 2 disposed under the grip 1 and having a diameter greater than that of the grip 1, and a dilating part 3-4 disposed under the stopper 2. Here, the dilating part 3-4 includes a dilator 32-4 reduced in diameter toward a lower portion thereof and having an inverted conic shape with a sharp tip, and a blade 31 disposed on both sides of the dilator 32-4 and being sharp toward the outside.

In a related-art bone tissue dilating apparatus, since a bone tissue has to be incised such that a thickness of adding a movement expanding piece can be inserted, it takes time to perform an implant operation. Also, since it takes time to heal an incised tissue, minimum bone tissues have been incised.

When an implant operation is performed on an alveolar bone, there should be an alveolar bone wide enough to perform the implant operation. When the width of the alveolar bone of a patient is too small to perform implant, the alveolar bone may be incised by a chisel, and then a gap created by the chisel is expanded by a dilator (spreader or an osteotome) to expand the alveolar bone.

In a related-art technology described above, however, there is an inconvenience in that two tools such as chisel and dilator (spreader, and osteotome) are needed and two or more different processes have to be performed. In an implant operation according to an embodiment of the present invention, an integrated alveolar bone dilating apparatus for dental implant may be used. The integrated alveolar bone dilating apparatus may be an integrated tool that incises a bone using only a single tool integrating a chisel for incising an alveolar bone and a dilator for expanding the incised bone and maintains a dilated state of the bone tissue.

Figure 1:
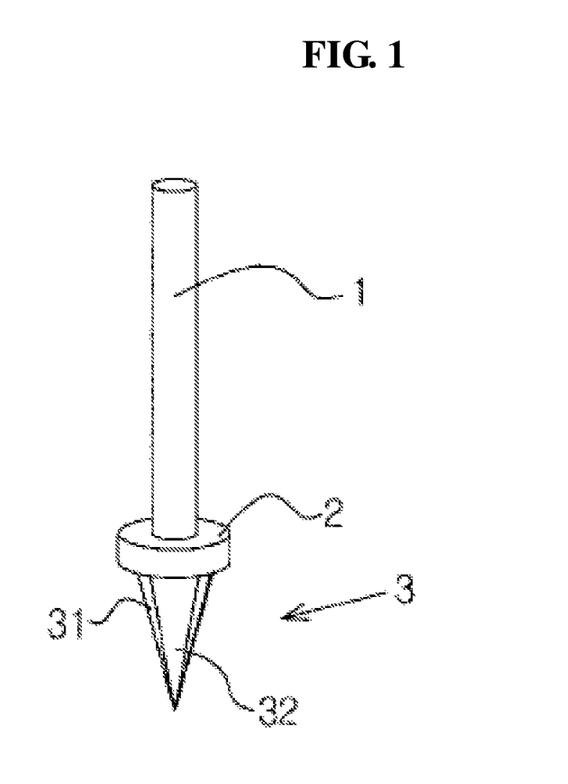
FIG. 1 is a view illustrating an exemplary integrated alveolar bone incision dilating apparatus for dental implant according to an embodiment of the present invention.
Figure 2:
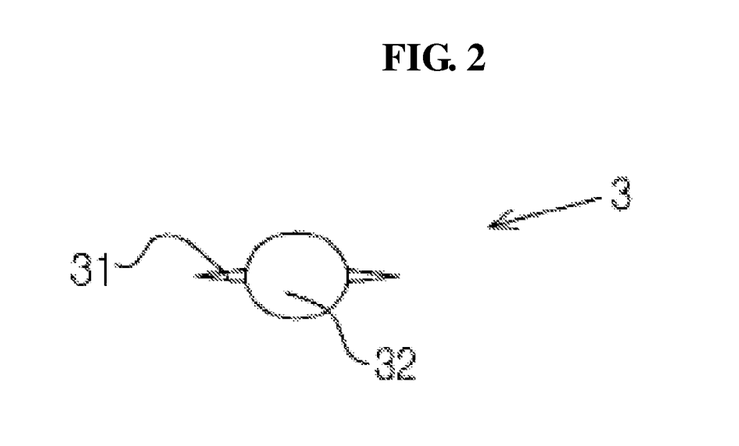
FIG. 2 is a side cross-sectional view illustrating an integrated alveolar bone incision dilating apparatus for dental implant according to an embodiment of the present invention.

FIGS. 1 and 2 illustrate an integrated alveolar bone dilating apparatus for mandibular anterior tooth implant. According to the location of a tooth and the width of an alveolar bone, since an alveolar bone of a mandibular anterior tooth has a uniform width and the bone slope is small, the shape shown in FIG. 1 may be appropriate.

Figure 3:
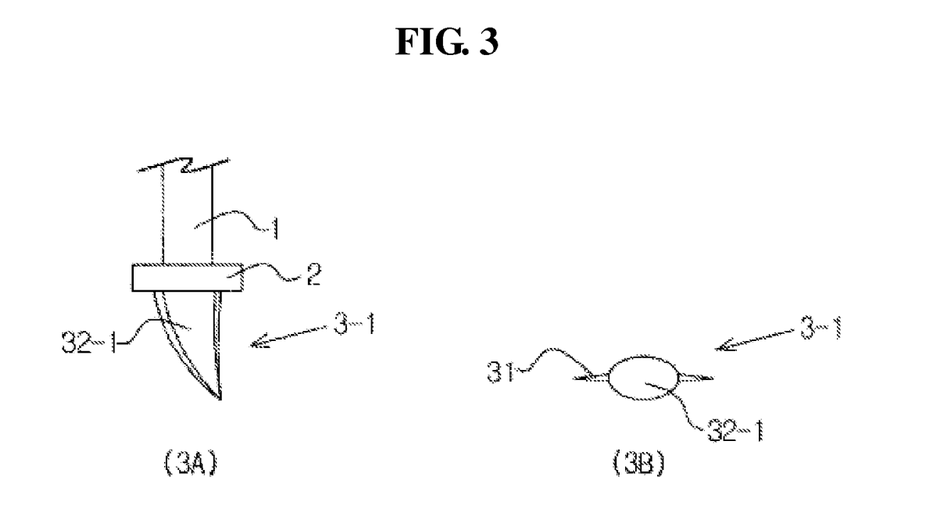
FIGS. 3 through 11 are views illustrating another exemplary integrated alveolar bone incision dilating apparatus for dental implant according to an embodiment of the present invention.

FIG. 3 illustrates an integrated alveolar bone dilating apparatus for maxillary anterior tooth implant. Since the alveolar bone of upper anterior teeth (center of upper teeth) mostly projects forward, the conic shape shown in FIG. 3, which is slightly curved in consideration of the slope of the alveolar bone of the upper teeth, may be appropriate.

Figure 4:
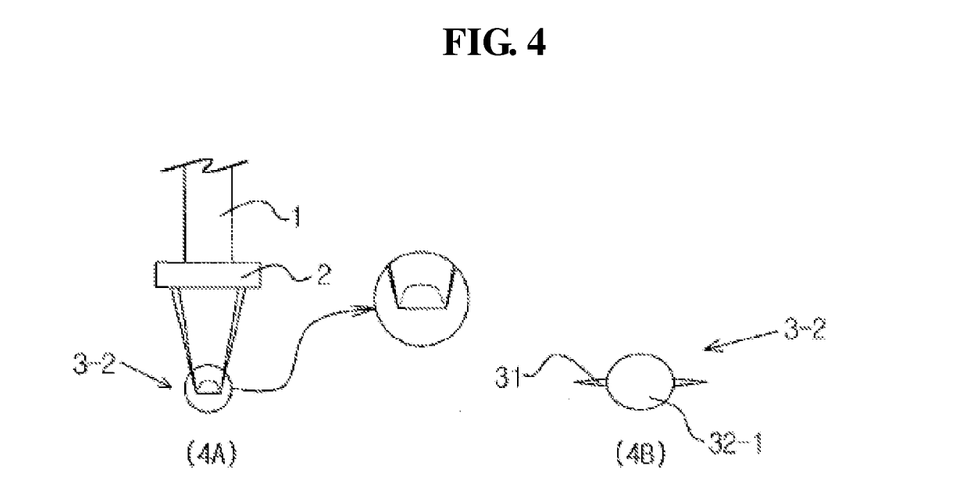

FIG. 4 illustrates an integrated alveolar bone dilating apparatus for maxillary molar implant. Since the alveolar bone can be expanded in concurrence with lifting of the maxillary sinus, and the tip of the apparatus has a round and circular blade, it can serve to cut and lift a cortical bone under the maxillary sinus (which is a cavity over the alveolar bone of the maxillary molar and affect breathing when pus is filled therein due to sinusitis).

Figure 5:
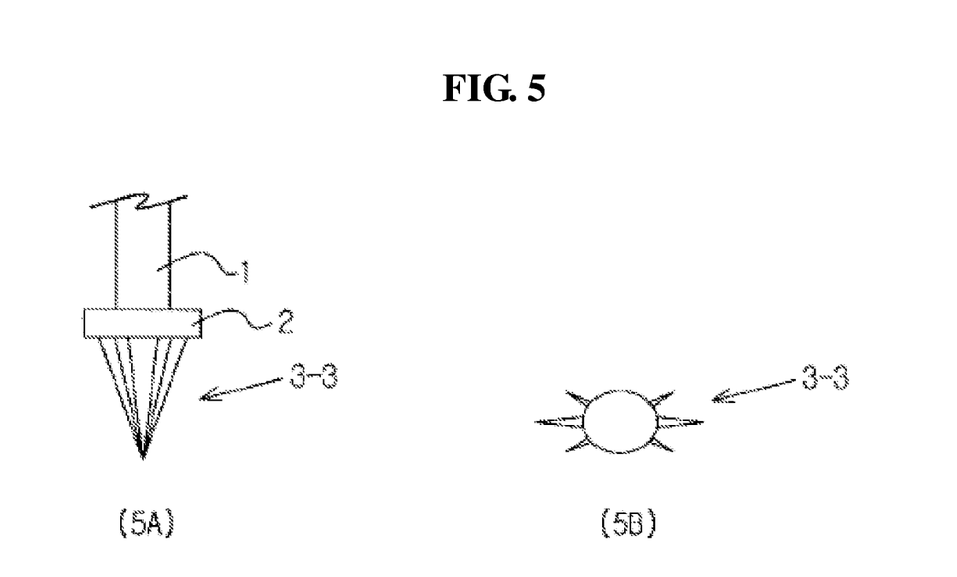

FIG. 5 illustrates an integrated alveolar bone dilating apparatus for mandibular molar implant. The alveolar bone may be cut in different directions, and may be progressively dilated at once. The integrated alveolar bone dilating apparatus has been improved to safely perform dilation by distributing a pressure applied to the alveolar bone. The integrated alveolar bone dilating apparatus may include about six blades to prevent fracture (damage) of a cortical bone.

Figure 6:
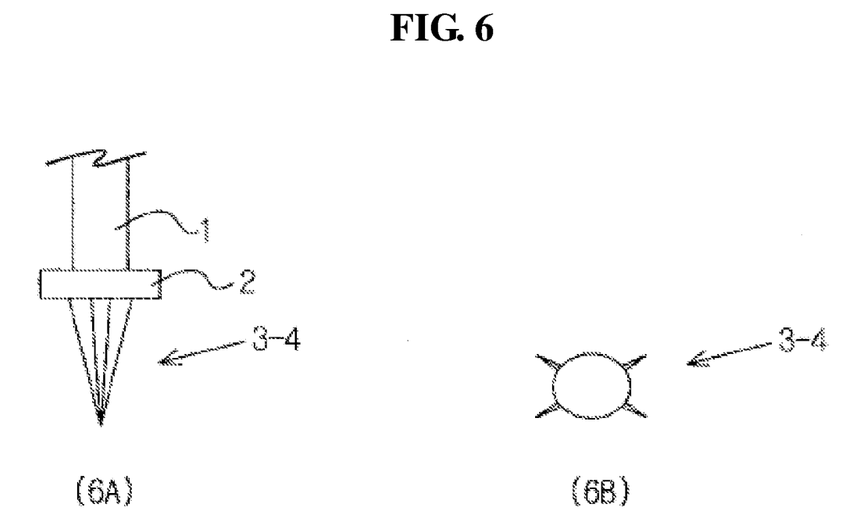
Figure 7:
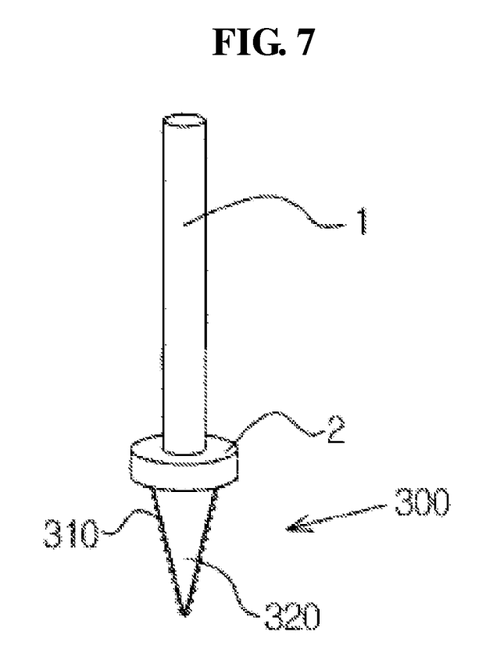
Figure 8:
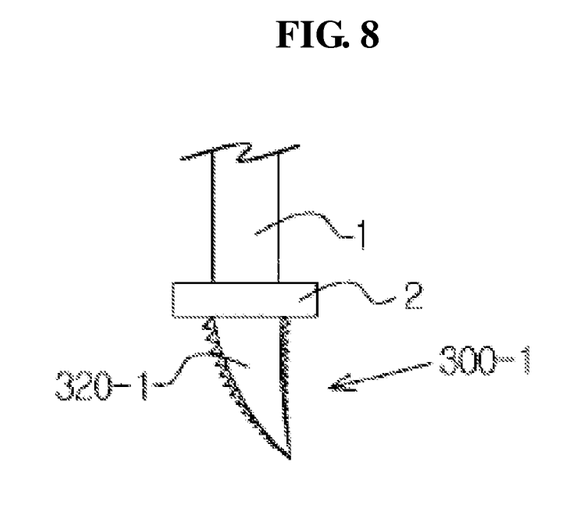
Figure 9:
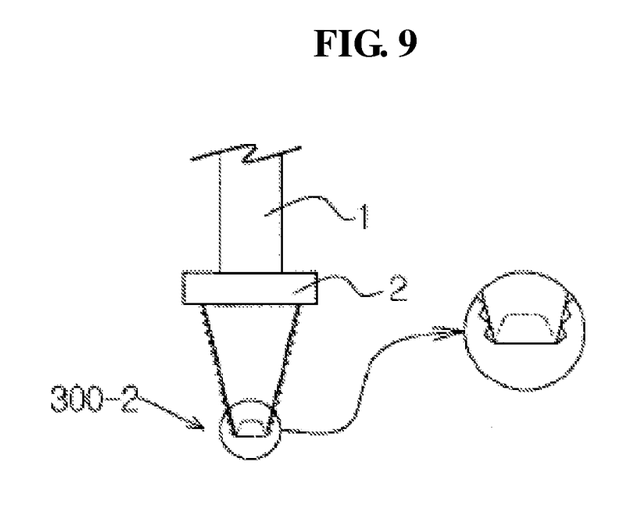
Figure 10:
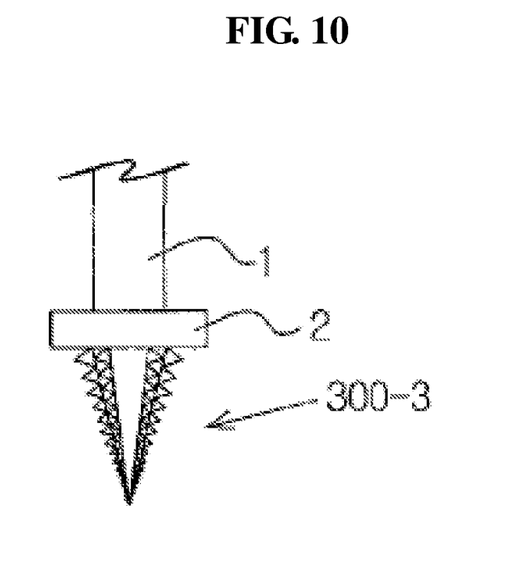
Figure 11:
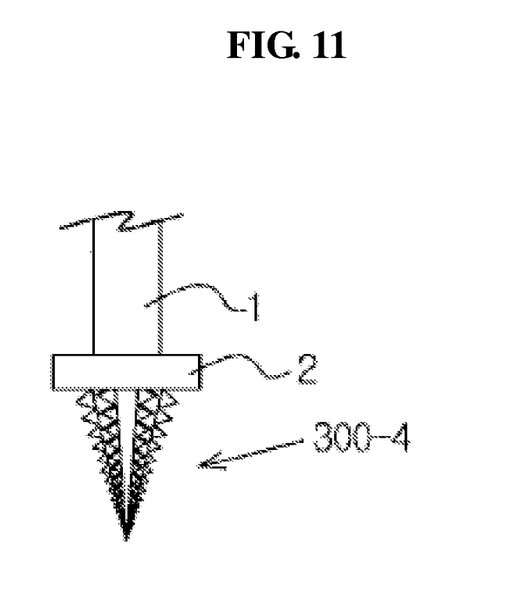

FIG. 6 illustrates an integrated alveolar bone dilating apparatus for single-tooth edentulous implant. The apparatus may be used when the width of the alveolar bone to be treated is smaller than the width of surrounding alveolar bones.

Hereinafter exemplary embodiments of the present invention will be described in detail with reference to the accompanying drawings.

FIG. 1 is a view illustrating an exemplary integrated alveolar bone incision dilating apparatus for dental implant according to an embodiment of the present invention. FIG. 2 is a side cross-sectional view illustrating an integrated alveolar bone incision dilating apparatus for dental implant according to an embodiment of the present invention. FIGS. 3 through 11 are views illustrating another exemplary integrated alveolar bone incision dilating apparatus for dental implant according to an embodiment of the present invention.

As shown in FIGS. 1 and 2, an integrated alveolar bone dilating apparatus for mandibular anterior tooth implant may include a grip 1 having a cylindrical shape, a stopper 2 disposed under the grip 1 and having a diameter greater than a diameter of the grip 1, and a dilating part 3 disposed under the stopper 2.

Here, the dilating part 3 may include a dilator 32 reduced in diameter toward a lower portion thereof and having an inverted conic shape with a sharp tip, and two blades 31 disposed on both sides of the dilator 32 and being sharp toward the outside.

As shown in FIG. 3, an integrated alveolar bone dilating apparatus for maxillary anterior tooth implant may include a grip 1 having a cylindrical shape, a stopper 2 disposed under the grip 1 and having a diameter greater than a diameter of the grip 1, and a dilating part 3-1 disposed under the stopper 2.

Here, the dilating part 3-1 includes a dilator 32-1 reduced in diameter toward a lower portion thereof and having an oval shaped diameter, an inverted conic shape with a sharp tip and one side curved and the other side straight, and two blades 31 disposed on both sides of the dilator 32-1 and being sharp toward the outside.

As shown in FIG. 4, an integrated alveolar bone dilating apparatus for maxillary molar implant may include a grip 1 having a cylindrical shape, a stopper 2 disposed under the grip 1 and having a diameter greater than a diameter of the grip 1, and a dilating part 3-2 disposed under the stopper 2.

Here, the dilating part 3-2 may include a dilator 32-2 reduced in diameter toward a lower portion thereof and having an inverted conic shape with a recessed tip and a blade-shape circular rim, and two blades 31 disposed on both sides of the dilator 32-2 and being sharp toward the outside.

As shown in FIG. 5, an integrated alveolar bone dilating apparatus for mandibular molar implant may include a grip 1 having a cylindrical shape, a stopper 2 disposed under the grip 1 and having a diameter greater than a diameter of the grip 1, and a dilating part 3-3 disposed under the stopper 2, Here, the dilating part 3-3 includes a dilator 32-3 reduced in diameter toward a lower portion thereof and having an inverted conic shape with a sharp tip, and six blades 31 disposed on a rim of the dilator 32-3 and being sharp toward the outside.

As shown in FIG. 6, an integrated alveolar bone dilating apparatus for single-tooth edentulous implant may include a grip 1 having a cylindrical shape, a stopper disposed under the grip 1 and having a diameter greater than a diameter of the grip 1, and a dilating part 3-4 disposed under the stopper 2, Here, the dilating part 3-4 includes a dilator 32-4 reduced in diameter toward a lower portion thereof and having an inverted conic shape with a sharp tip, and four blades 31 disposed on both sides of the dilator 32-4 and being sharp toward the outside.

As shown in FIGS. 7 through 11, the blade 31 may have a saw-toothed shape instead of a straight shape.

Hereinafter, the usage and the operation state of an integrated alveolar bone incision dilating apparatus for dental implant according an embodiment of the present invention will be described.

First, a tooth may be removed, and then a grip 1 of an integrated alveolar bone incision dilating apparatus for dental implant may be grasped by the hand. Thereafter, when a strength (pressure) is applied to the top of the grip 1 by a hammer, an alveolar bone may be incised by a blade 31 of a dilator, and simultaneously, the incised alveolar bone may be expanded by a dilating part 32, 32-1, 32-2, 32-3 and 32-4 of the dilator 3, 3-1, 3-2, 3-3 and 3-4. When the alveolar bone is expanded to a certain width, an implant may be fixed in the expanded part, and other surrounding bones may be transplanted and arranged to perform an implant operation.

INDUSTRIAL APPLICABILITY

According to an embodiment of the present invention, an integrated alveolar bone dilating apparatus for dental implant may be used. The integrated alveolar bone dilating apparatus may be an integrated tool that incises a bone using only a single tool integrating a chisel for incising an alveolar bone and a dilator for expanding the incised bone and maintains a dilated state of the bone tissue.

The invention claimed is:

1. An integrated alveolar bone dilating apparatus for a dental implant, comprising:
    a cylindrical shaped grip;
    a stopper connected to the grip, wherein the stopper has an upper surface and a diameter greater than a diameter of the grip;
    a dilating part including a conic shaped dilator and two blades, the dilating part being connected to the stopper, wherein the diameter of the stopper is greater than an oval shaped diameter of the conic shaped dilator when taken in a horizontal cross-section parallel to the upper surface of the stopper,
    wherein the conic shaped dilator includes the oval shaped diameter being linearly reduced along an entire length of the dilator, and the two blades are symmetrically disposed on a circumference surface of the entire length of the dilator and protrude outward from the circumference surface, and
    wherein, when taken in the horizontal cross-section, the oval shaped dilator has a first point, a second point, a third point opposite the first point, and a fourth point opposite the second point located on the circumference surface, wherein a first blade of the two blades has a first end point, a first straight line extending outward from the first point and a second straight line extending outward from the second point and meeting with the extended first straight line at the first end point, and wherein a second blade of the two blades has a second end point opposite the first end point, a third straight line extending outward from the third point and a fourth straight line extending outward from the second point and meeting with the extended third straight line at the end point.

2. An integrated alveolar bone dilating apparatus for a dental implant, comprising:
    a cylindrical shaped grip;
    a stopper connected to the grip, wherein the stopper has an upper surface and a diameter greater than a diameter of the grip; and
    a dilating part including a horn shaped dilator and two blades, the dilating part being connected to the stopper, wherein the diameter of the stopper is greater than an oval shaped diameter of the horn shaped dilator when taken in a horizontal cross-section parallel to the upper surface of the stopper,
    wherein the horn shaped dilator includes the oval shaped diameter at one end of the dilator being gradually reduced toward an opposite end of the dilator, the opposite end being formed with a sharp tip,
    wherein the dilator has two portions symmetrically disposed along an entire length of the dilator when taken in horizontal cross-section, one portion being straightly disposed and the other symmetrical portion being convexly disposed, and the two blades are symmetrically disposed on the two symmetrical portions along the entire length of the dilator when taken in horizontal cross-section and being sharply projected outward from the two portions, and
    wherein, when taken in the horizontal cross-section, the oval shaped dilator has a first point, a second point, a third point opposite the first point, and a fourth point opposite the second point located on the circumference surface, wherein a first blade of the two blades has a first end point, a first straight line extending outward from the first point and a second straight line extending outward from the second point and meeting with the extended first straight line at the first end point, and wherein a second blade of the two blades has a second end point opposite the first end point, a third straight line extending outward from the third point and a fourth straight line extending outward from the second point and meeting with the extended third straight line at the end point.

* * * * *